US008436042B2

(12) United States Patent
Selifonov

(10) Patent No.: US 8,436,042 B2
(45) Date of Patent: May 7, 2013

(54) ADDUCTS OF LEVULINIC DERIVATIVES WITH EPOXIDIZED FATTY ACID ESTERS AND USES THEREOF

(75) Inventor: Sergey Selifonov, Plymouth, MN (US)

(73) Assignee: Segetis, Inc., Golden Valley, MN (US)

(*) Notice: Subject to any disclaimer, the term of this patent is extended or adjusted under 35 U.S.C. 154(b) by 656 days.

(21) Appl. No.: 11/993,212

(22) PCT Filed: Nov. 22, 2006

(86) PCT No.: PCT/US2006/045273
§ 371 (c)(1),
(2), (4) Date: Aug. 2, 2010

(87) PCT Pub. No.: WO2007/062158
PCT Pub. Date: May 31, 2007

(65) Prior Publication Data
US 2010/0292373 A1    Nov. 18, 2010

Related U.S. Application Data

(60) Provisional application No. 60/739,022, filed on Nov. 22, 2005.

(51) Int. Cl.
*C08K 5/151*    (2006.01)
*C07D 317/24*    (2006.01)

(52) U.S. Cl.
USPC ........... 514/467; 549/448; 549/454; 524/108; 524/111; 524/317; 554/148; 554/213

(58) Field of Classification Search .................. 514/467; 549/448, 454; 524/108, 111, 317; 554/148, 554/213
See application file for complete search history.

(56) References Cited

U.S. PATENT DOCUMENTS

| 2,492,692 | A | * | 12/1949 | Drake et al. .................. 549/454 |
| 2,654,723 | A | | 10/1953 | Greene |
| 2,768,212 | A | | 10/1956 | Copenhaver |
| 2,838,467 | A | | 6/1958 | Dobay |
| 2,985,536 | A | | 5/1961 | Stein et al. |
| 3,336,370 | A | | 8/1967 | Dill |
| 4,153,064 | A | * | 5/1979 | Sawada et al. ................ 131/343 |
| 4,841,075 | A | | 6/1989 | Matsushita et al. |
| 4,857,607 | A | | 8/1989 | Cotting et al. |
| 4,908,406 | A | | 3/1990 | Mulhaupt et al. |
| 5,608,105 | A | | 3/1997 | Fitzpatrick |
| 6,797,753 | B2 | | 9/2004 | Benecke et al. |
| 7,153,996 | B2 | | 12/2006 | Fagan et al. |
| 8,053,468 | B2 | * | 11/2011 | Selifonov ...................... 514/467 |
| 2006/0264568 | A1 | * | 11/2006 | Pajerski ........................ 524/591 |
| 2008/0154053 | A1 | * | 6/2008 | Erhan et al. ................... 554/149 |
| 2008/0242721 | A1 | * | 10/2008 | Selifonov ...................... 514/467 |

FOREIGN PATENT DOCUMENTS

| JP | 2804327 A | 9/1953 |
| JP | 4217972 A | 8/1992 |
| JP | 7163382 A | 6/1995 |
| JP | 2004168812 A | 6/2004 |
| WO | WO 2007062118 A2 * | 5/2007 |

OTHER PUBLICATIONS

Horsfall et al. Fungitoxicity of Dioxanes, Dioxolanes and methylenedioxybenzenes, 1965.*
Biswas et al., "Synthesis of Diethylamine-Functionalized Soybean Oil." *J. Agric. Food Chem.* (2005) 53, 9485-9490.
Blackett et al., "The Mechanism of 1,3-Dioxolane Formation from the $BF_3$ Catalysed Reaction of Epoxides with Carbonyl Compounds." *Tetrahedron* (1970) 26, 1311-1313.
Blee et al., "Soybean Epoxide Hydrolase: Identification of the Catalytic Residues and Probing of the Reaction Mechanism with Secondary Kinetic Isotope Effects." *Journal of Biological Chemistry* (2004) JBC Papers in Press, Published Dec. 13, 2004 as Manuscript M411366200.
Blunt et al., "Reactions of Epoxides IX the Boron Trifluoride Catalysed Rearrangement of Some 3,3-Ethylenedioxy-5,6-Epoxycholestanes." *Tetrahedron* (1996) 22, 1421-1429.
Clerici et al., "Efficient Acetalisation of Aldehydes Catalyzed by Titanium Tetrachloride in a Basic Medium." *Tetrahedron* (1998) 54, 15679-15690.
Condea, "All About Fatty Alcohols." (2000) Online at fatty.alcohols@condea.de.
DiSerio et al., "Transesterification of Soybean Oil to Biodiesel by Using Heterogeneous Basic Catalysts." *Ind. Eng. Chem. Res.* (2006) 45, 3009-3014.
Doll et al., "Synthesis of Cyclic Acetals (Ketals) from Oleochemicals Using a Solvent Free Method." *Green Chem.* (2008) 10, 712-717.
Doll, et al., "Synthesis of Branched Methyl Hydroxy Stearates Including an Ester from Bio-Based Levulinic Acid." *Ind. Eng. Chem. Res.* (2007), 46, 11, 3513-3519.
Du et al., "Catalytic Epoxidation of Methyl Linoleate." *JAOCS* (2004) 81, 4.
Environmental Grantmakers Association 2006, "Biofuels: Opportunity or Threat?" supplement to the Midwest Funders Policy Briefing 2006: The Opportunities and Threats of Biofuels, held in Minneapolis, Minnesota.
Gevorkyan et al., "Tetrafluoroboric Acid—A New Catalyst for the Synthesis of 1,3-Dioxolanes. Preparation of Hydroxyacetone." *Khimiya Geterotsiklicheskikh Soedinenii*, No. 1, pp. 33-36, Jan. 1991. Original article submitted Nov. 12, 1989.
Girisuta, "Levulinic Acid from Lignocellulosic Biomass." Ph.D. Thesis, University of Groningen, Nov. 5, 2007, ISBN 978-90-367-3228-4.

(Continued)

*Primary Examiner* — Mark Kaucher
(74) *Attorney, Agent, or Firm* — Cantor Colburn LLP

(57) ABSTRACT

The present disclosure relates to methods of preparation of compounds resulting from the reaction of levulinic esters and epoxidized unsaturated fatty acid esters. The compounds are useful as renewable biomass-based plasticizers for a variety of polymers. Mono-, di- and tri-ketal adducts formed in a reaction between alkyl esters of levulinate and epoxidized unsaturated fatty acid esters derived from vegetable oils are also disclosed.

12 Claims, 9 Drawing Sheets

OTHER PUBLICATIONS

Gonzalez et al., "Application of Fourier Transform Infrared Spectroscopy in the Study of Interactions Between PVC and Plasticizers: PVC/Plasticizer Compatibility versus Chemical Structure of Plasticizer." *J. Appl. Pol. Sci.* (2006) 101, 1731-1737.

Hanzlik, et al., "Reactions of Epoxides and Carbonyl Compounds Catalyzed by Anhydrous Copper Sulfate." *J. Org. Chem.* (1978) 43, 3.

Hollingsworth, "Progress Report for the Center for Renewable Resource Chemistries 2007." Online at < http://www.msu.edu/~vprgs/funding/crm1.pdf>.

Hoydonckx et al., "Esterification and Transesterification of Renewable Chemicals." *Topics in Catalysis* (2004) 27, 1-4.

Jain et al., "Fatty Acid Based Biodegradable Polymer." *Polymer Reviews* (2008) 48, 156-191.

Jay, "Direct Titration of Epoxy Compounds and Aziridines." *Analytical Chemistry* (1964) 36, 3.

Keenan et al., "Production and Characterization of Poly-β-hydroxyalkanoate Copolymers from *Burkholderia cepacia* Utilizing Xylose and Levulinic Acid." *Biotechnol. Prog.* (2004) 20, 1697-1704.

Kim et al., "Transesterification of Vegetable Oil to Biodiesel Using Heterogeneous Base Catalyst." *Catalysis Today* (2004) 93(95), 315-320.

Koeners et al., "Synthesis of Oligosaccharides by Using Levulinic Ester as an Hydroxyl Protecting Group." *Tetrahedron Letters.* (1980) 21, 381-382.

Lee et al., "Copper(II)-catalyzed Formation of 1,3-Dioxolanes from Oxiranes." *Bull. Korean Chem. Soc.* (2005) 26(2), 221-222.

Lee et al., "N-Benzyl Pyridinium Salts as New Useful Catalysts for Transformation of Epoxides to Cyclic Acetals, Orthoesters, and Orthocarbonates." *Chemistry Letters* (1990) 2019-2022.

Li et al., "Efficient and Highly-selective Cycloaddition of Epoxides with Carbonyl Compound Over Wells-Dawson Type Heteropolyacids." *Journal of Molecular Catalysis A: Chemical* (2005) 236, 72-76.

Lindblad et al., "Polymers from Renewable Resources." *Advances in Polymer Science* (2002) 157.

Ma et al., "Biodiesel Production: A Review." *Bioresource Technology* (1999) 70, 1-15.

Meltzer et al., "2,2-Disubstituted 1,3-Dioxolanes and 2,2-Disubstituted 1,3-Dioxanes." *J. Org. Chem.* (1960) p. 712-715.

Meskens, "Methods for the Preparation of Acetals from Alcohols or Oxiranes and Carbonyl Compounds." *Synthesis* (1981) 501-522.

Evans et al., "River Valley Biomass Refinery Market Study, Final Report." report by MicroChem Technologies Inc. under U.S. Department of Energy Award No. DE-FG36-04G014246 (Mar. 26, 2006).

Moncrieff ,"Ketals." *JAOCS* (Aug. 1947) p. 259-261.

Muturi et al., "Epoxidized Vegetable Oils as Reactive Diluents I. Comparison of Vernonia, Epoxidized Soybean and Epoxidized Linseed Oils." *Progress in Organic Coatings* (1994) 25, 85-94.

Nahmany et al., "Chemoselectivity in Reactions of Esterification." *Org. Biomol. Chem.* (2004) 2, 1563-1572.

"New Twist on Green: 2008 Ford Mustang Seats Will Be Soy-Based Foam." Online at <www.edmunds.com/insideline/do/News/articleId>.

Natl. Renewable Energy Laboratory, NREL/BR-510-39436, "From Biomass to Biofuels" (Aug. 2006).

Ono et al., "Preparation, Surface-Active Properties and Acid Decomposition Profiles of a New 'Soap' Bearing a 1,3-Dioxolane Ring." *JAOCS* (1993) 70, 1.

Otera, J, *Esterification*, Wiley-VCH, Germany, 2003.

Parreira et al., "Quantitative Determination of Epoxidized Soybean Oil Using Near-Infrared Spectroscopy and Multivariate Calibration." *Applied Spectroscopy* (2002) 56, 12.

Paterson et al., "Studies Towards the Synthesis of the Zaragozic Acids: A Novel Epoxide Cyclisation Approach to the Formation of the Bicyclic Acetal Core." *Tetrahedron Letters* (1996) 37(48) 8803-8806.

Petrovic et al., "Polyester Polyols and Polurethanes from Ricinoleic Acid." *Journal of Applied Polymer Science* (2008) 108, 1184-1190.

"Cargill's BiOH Polyols Business Opens Manufacturing Site Brazil." *PU Magazine* (Sep. 26, 2007) Online at http://www.pu-magazine.com/index.php?id=177&tt_news=4157.

Rios, et al., "Textural and Chemical Characterization of Crystalline Ti-SiO$_2$ Catalysts Used in the Epoxidation of Fatty Esters." DYNA, Universidad Nacional de Colombia (2006) 73(148), 95-101. ISSN: 0012-7353.

Samuelsson et al., "A Study of Fatty Acid Methyl Esters with Epoxy or Alkyne Functionalities." *JAOCS* (2001) 78, 12.

Sanda et al., "Vinylcyclopropanone Cyclic Acetal—Synthesis, Polymerization, Structure of the Polymer and Mechanism of the Polymerisation." *Macromolecules* (1994) 27, 1099-1111.

Sarnacke, S., "Soy Beans as Polymer Building Blocks." Omni Tech International, Ltd. Presentation to United Soybean Board, Aug. 16, 2007.

Sato et al., "Kinetic Studies of Liquid-Phase Acetal Formation Catalyzed by Keggin-Type Heteropolyacids." *Journal of Molecular Catalysis A: Chemical* (1996) 114, 209-216.

Sloan, "Bio-Composites Update: Bio-Based Resins Begin to Grow." (Apr. 2008) Online at http://compositesworld.com/ct/issues/2008/April/112792.

"A Survey of Recent Chemical Price Trends." Omni Tech International, Ltd., report prepared for the United Soybean Board (Dec. 2005).

Srivastava et al., "Synthesis, Characterization and Curing Behaviour of Partial Esters of Cycloaliphatic Epoxy Resins." *Designed Monomers and Polymers* (2005) 8(4), 319-334.

Suppes et al., "Calcium Carbonate Catalyzed Alcoholysis of Fats and Oils." *JAOCS* (2001) 78, 2.

Takenishi et al., "The Syntheses from Levulinic Acid. A Possible Use of Some 2 Methyl-5-Oxopyrrolidine-2-Carboxylic Esters as Plasticizers." Bulletin of the Chemical Society of Japan (1954) 27(4), 207-209.

Timokhin et al., "Levulinic Acid in Organic Synthesis." *Russian Chemical Reviews* (1999) 68 (1) 73-84.

Torok et al., "1,3-Dioxolane Formation via Lewis Acid-Catalyzed Reaction of Ketones with Oxiranes." *J.Org. Chem.* (1993) 58, 7274-7276.

Tu et al., "Physical Properties of Water-Blown Rigid Polyurethane Foams from Vegetable Oil-Based Polyols." *J. Appl.Pol. Sci.* (2007) 105, 453-459.

Yasuda et al., "Cyclic Carbonate Synthesis from Supercritical Carbon Dioxide and Epoxide over Lanthanide Oxychloride." AIST (2002) Online at <www.paper.edu.cn>.

Zhang et al., "Effect of Different Isocyanates on the Properties of Soy-Based Polurethanes." *Journal of Applied Polymer Science* (2003) 88, 2912-2916.

\* cited by examiner

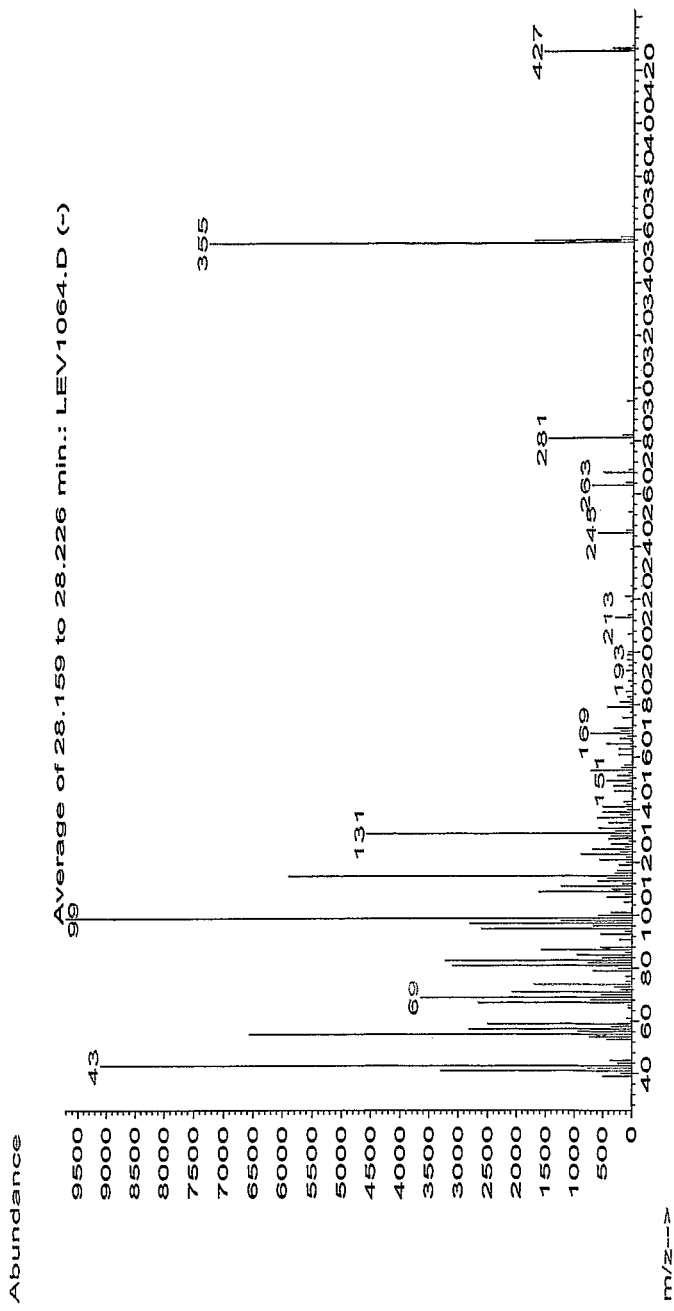
FIGURE 2A₁

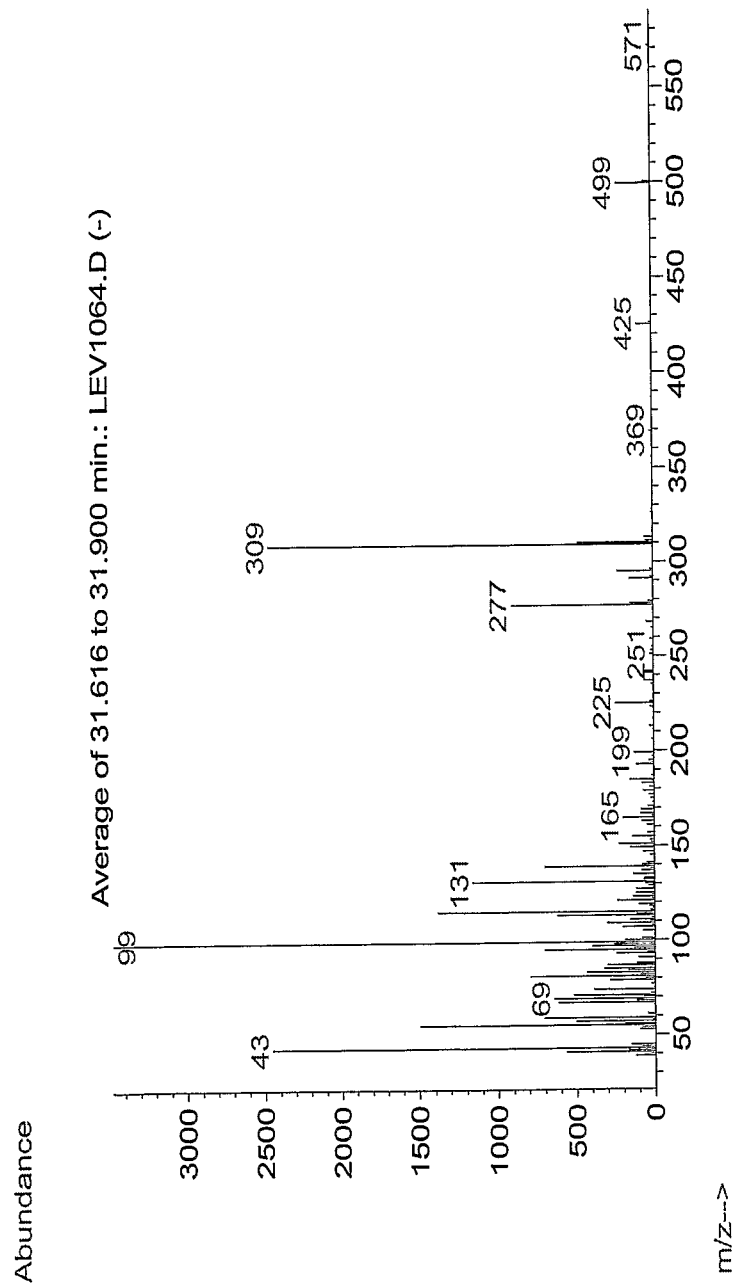
FIGURE 2A₂

ADDUCTS OF LEVULINIC DERIVATIVES WITH EPOXIDIZED FATTY ACID ESTERS AND USES THEREOF

CROSS-REFERENCE TO RELATED APPLICATIONS

This application is a National Stage application under 35 U.S.C. §371 to International Application No. PCT/US2006/045273 having an International Filing Date of Nov. 22, 2006, which claims benefit under 35 U.S.C. §119(e) to U.S. Provisional Application No. 60/739,022 filed on Nov. 22, 2005, both of which are incorporated by reference in their entirety herewith.

TECHNICAL FIELD

The present disclosure relates to methods of preparation of compounds from levulinic esters and epoxidized unsaturated fatty acid esters. The compounds are useful as renewable biomass-based plasticizers for a variety of polymers.

BACKGROUND

Plasticizers for various polymers are widely known in the art. Most of the plasticizing compounds are produced from petroleum-derived feedstocks that are expensive and non-renewable. Certain plasticizer compounds are prepared from reviewable raw materials such as triglycerides of vegetable oils, typically by epoxidation of unsaturated fatty acid fragments. However, epoxidized triglycerides have significant limitations and cannot be satisfactorily used as primary plasticizers, because their compatibility with poly(vinyl chloride) (PVC) polymers is limited.

Certain esters of aliphatic dicarboxylic acids such as esters of sebacic and azelaic acids are produced from various unsaturated fatty acid compounds. Such dicarboxylic acids have excellent plasticizing properties. However, due to the complexity of synthesis involved or raw material costs, such dicarboxylic acids are relatively expensive and used as premium products in applications intended for use at low temperatures.

Certain known plasticizer compounds used in industrial practice, such as esters of phosphoric acid and alkylated phenols, are harmful to the environment and confer unpleasant odors to finished products and cause harmful air pollution.

Commonly used in plasticizing PVC, esters of phthalic acid have been recently implicated as endocrine disruptors responsible for harmful reproductive effects in animals and humans, and for male reproductive toxicity in humans, in particular.

It is therefore desirable to provide plasticizing compounds that are inexpensive, non-toxic, made from renewable abundant raw materials, and have environmental breakdown products substantially devoid of harmful effects.

SUMMARY

Ester compounds are disclosed that are versatile plasticizers with good compatibility with many polymers. The ester compounds are produced from abundant and inexpensive renewable materials such as unsaturated fatty acid esters and levulinic acid esters. Epoxide groups of monoepoxidized unsaturated fatty acid esters are reacted with levulinic esters in the presence of a suitable catalyst, typically a protic acid or a Lewis acid, to form ketals of levulinic esters of dihydroxylated fatty acid esters. Similarly, levulinic acid esters react with bis-epoxidized and tris-epoxidized unsaturated fatty acid esters derived from unsaturated fatty acid esters having two or three double bonds, thereby yielding corresponding bis-ketals and tris-ketals. Additionally, levulinic acid and angelicalactone can be used in combination or in place of levulinic acid ester in reactions with epoxidized unsaturated fatty acid esters. Adducts of levulinic acid ester and epoxidized unsaturated fatty acid are useful as plasticizers for a range of industrial polymers.

Examples of compounds prepared from levulinic acid ester, levulinic acid, and/or angelicalactone and an epoxidized unsaturated fatty acid can include the formula:

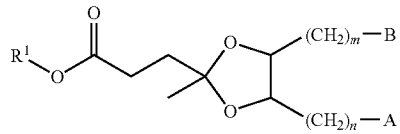

and the formula:

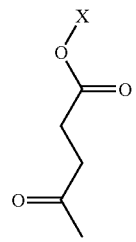

wherein X is selected from the following:

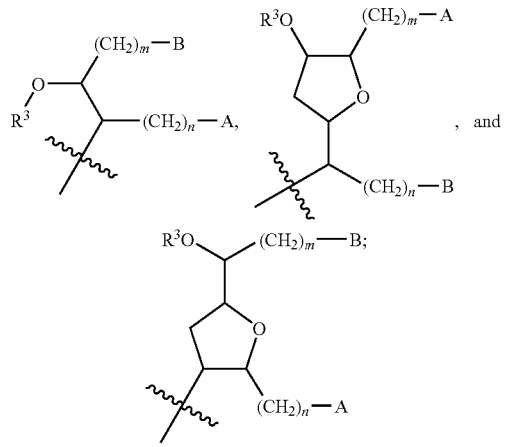

and wherein $R^1$ and $R^3$ are independently a $C_1$-$C_{10}$ linear or branched alkyl or alkoxyalkyl; one of A or B is hydrogen and the other is an esterified carboxy group; and n and m are independently integers from 0 to 20, and the value of the sum of m+n is in the range from 8 to 21.

The reaction product can also have the formula:

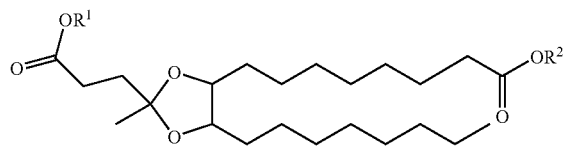

wherein $R^1$ and $R^2$ are independently a $C_1$-$C_{10}$ linear or branched alkyl or alkoxyalkyl.

When levulinic acid ester, levulinic acid, and/or angelicalactone are reacted with a bis-epoxidized or tris-epoxidized unsaturated fatty acid ester, examples of the resulting compounds can include the following:

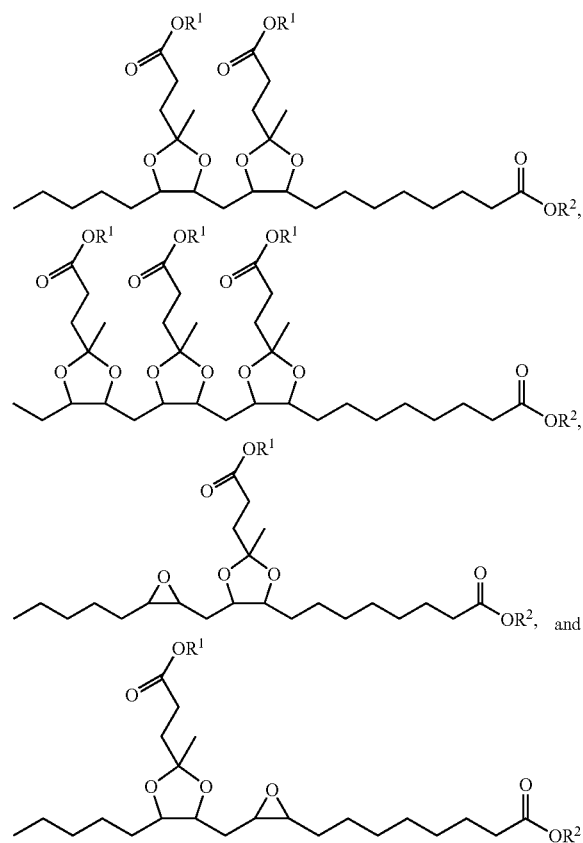

wherein $R^1$ and $R^2$ are independently a $C_1$-$C_{10}$ linear or branched alkyl or alkoxyalkyl. In some embodiments, $R^1$ and $R^2$ can be methyl, ethyl, n-butyl, isobutyl, isoamyl, or 2-ethylhexyl.

The compounds can also be used as a plasticizer with a base polymer in a plasticized polymer composition. A base polymer can include vinyl chloride polymers, poly(3-hydroxyalkanoates), poly(lactates), and polysaccharide polymers.

The details of one or more embodiments of the invention are set forth in the accompanying drawings and the description below. Other features, objects, and advantages of the invention will be apparent from the description and drawings, and from the claims.

DETAILED DESCRIPTION OF THE DRAWINGS

FIG. 1 demonstrates a representative EI mass-spectra of compounds (4) (FIG. 1A) and (11) (FIG. 1B), obtained in the course of GC-MS analysis, per Example 6. (Electron ionization at 70 eV).

FIG. 2A is a representative EI mass-spectra of compounds (4) (FIG. 2A$_1$) and (11) (FIG. 2A$_2$), obtained in the course of GC-MS analysis, per Example 7 (Sample B).

DETAILED DESCRIPTION

Figure 1A:
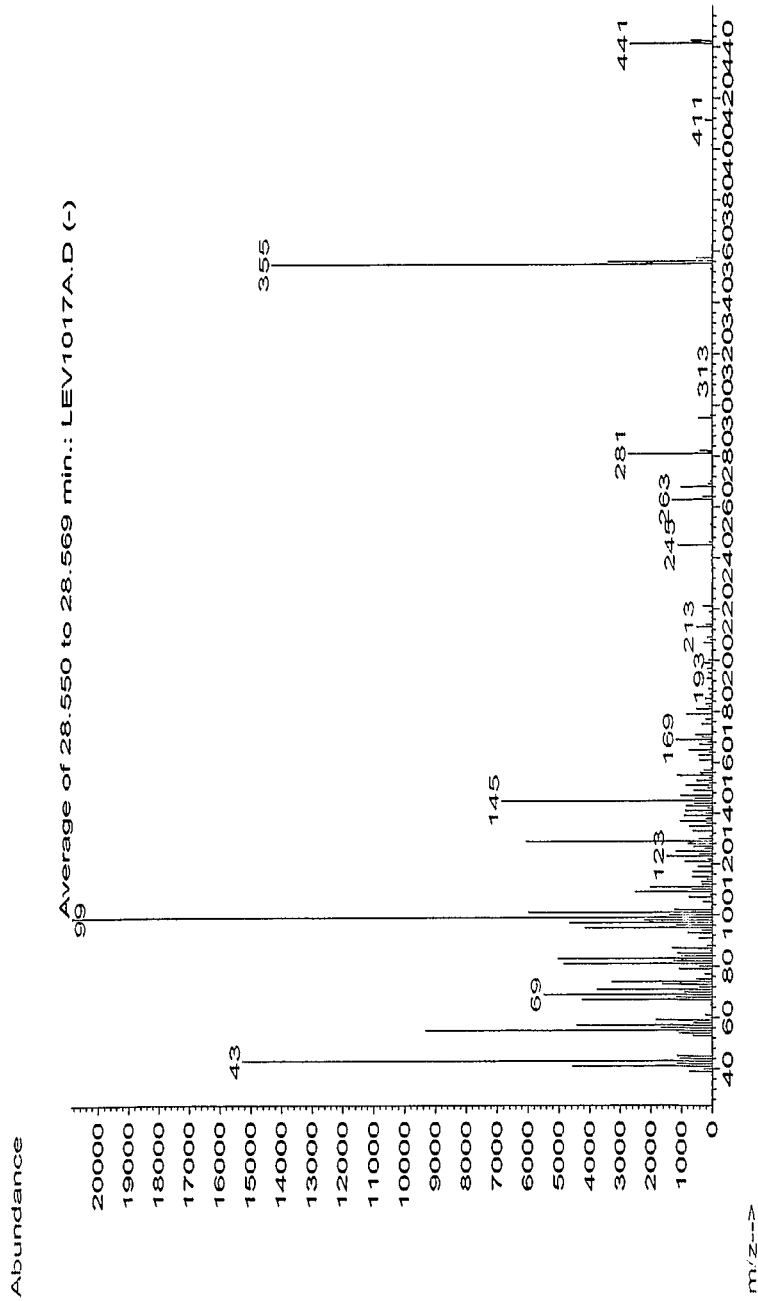

The following terms apply:

Unsaturated fatty acids mean linear monocarboxylic acids having from 10 to 24 carbon atoms and at least one double bond. The double bonds can be in any position, conjugated with each other or non-conjugated, but not in allenic arrangements, and any of the double bonds can be independently cis or trans. Preferably, unsaturated fatty acids have one to three double bonds. Fatty acids can also be composed of a mixture of various unsaturated and saturated fatty acids, for example, as in the triglycerides of various vegetable oils, fish oils, and palm oils.

Esters of unsaturated fatty acids mean esters of the above-described fatty acids with monohydric or with polyhydric alcohols.

Monohydric alcohols are linear or branched primary or secondary alkanols or alkoxyalkanols having from 1 to 12 carbon atoms. Preferred examples of alkanols are methanol, ethanol, propanol, isopropanol, butanol, secondary butanol, isobutanol, isoamyl alcohol, 2-ethylhexanol. Preferred alkoxyalkanols are primary or secondary alcohols having from 3 to 12 carbon atoms, wherein a linear, branched, or cyclic alkoxy group having from 1 to 8 carbon atoms is located at a vicinal position to the hydroxyl group. Such alkoxyalkanols are typically derived by opening an alkyl oxirane with an alkanol. Another suitable example of an alkoxyalkanol is tetrahydrofurfuryl alcohol readily accessible via hydrogenation of furfural. The most preferred are monohydric alcohols due to their availability, cost and satisfactory stability of their esters.

Polyhydric alcohols are linear or branched polyhydroxylated alkanes having from 1 to 6 hydroxyl groups. Typical examples are ethylene glycol, propylene 1,2- and 1,3-diols, butylene glycol isomers, glycerol, 1,2,4-trihydroxybutane, pentaerythritol, xylitol, ribitol, sorbitol, mannitol, and galactitol. Polyhydric alcohols can optionally contain one or more ether bonds, and suitable examples of such polyhydric alcohols are isosorbide, sorbitane isomers, and diglycerol.

It is preferred that substantially all hydroxyl groups of the polyhydric alcohol are esterified with an unsaturated fatty acid group. It is understood that in the industrial practice it may not be practical to achieve a full esterification. It is also understood that in the industrial practice, where mixed fatty acid compositions are used, not all of the fatty acid groups can be unsaturated and some fully saturated fatty acid groups can be present. In fact, it is cost-advantageous to use mixtures of unsaturated and saturated fatty acid esters such as present in triglycerides of typical vegetable oils (e.g. soybean oil, linseed oil, canola oil, safflower oil, sunflower oil, corn oil, castor oil, their blends and the like). It is preferred, however, that the mixed fatty acid esters contain predominantly unsaturated fatty acid esters. It is also preferred that a fatty acid ester with a high content of mono-unsaturated fatty acid ester is used, such as compositions found in high oleic canola oil. Esters of 10-undecylenic acid are also preferred. Another preferred starting material is a mixture of methyl esters of fatty acids derived by trans-esterification of vegetable oils (e.g., of soybean oil, canola oil and other unsaturated triglycerides commonly used in the industrial production of various biodiesel fuels).

Various unsaturated fatty acid esters can be optionally blended, mixed, partially hydrogenated, or otherwise isomerized to change position or stereochemistry of the double bonds.

Epoxidized unsaturated fatty acid ester means that at least one of the double bonds of the unsaturated fatty acid ester is oxidized to an epoxy group. Such oxidations are well known in the art and can be readily accomplished in an industrial scale, e.g., by using hydrogen peroxide and a carboxylic acid (e.g., formate or acetate), or by the halohydrin method. It is preferred, however, that epoxidation of a majority or all of the double bonds present in the unsaturated fatty acid ester is accomplished. It is understood that in practice, epoxidized fatty acid esters may contain various quantities of by-products arising from hydrolysis or rearrangement of epoxides and from cross-linking of the fatty acid chains. Use of epoxidized fatty acid esters containing small quantities of epoxidation by-products and epoxide decomposition by-products is fully within the scope of the present disclosure.

Levulinic esters are esters of levulinic (4-oxopentanoic) acid and a monohydric alcohol. However, the monohydric alcohol fragment in the levulinic ester is selected independently from the monohydric alcohol fragment of the unsaturated fatty acid esters, and thus can be the same or different. Levulinic esters can optionally be mixtures of levulinic esters with more than one monohydric alcohol.

Polymers. Poly(vinyl chloride) polymers, PVC, are homopolymers or co-polymers of vinyl chloride. Many PVC compounds of various degree of polymerization, cross-linking and co-polymer composition are known in the art and are produced industrially.

Poly(3-hydroxyalkanoates), PHA, are polyester homopolymers or co-polymers of 3-hydroxyalkanoic acids. Preferably, PHA is composed of linear 3-hydroxyalkanoic fragments having from 3 to 18 carbon atom atoms. Poly(3-hydroxybutyrate), PHB, is a homopolymer that is produced biologically, for example by various microorganisms. A pure PHB polymer is a brittle polymer having a narrow range of processing temperatures, and it decomposes readily at temperatures that are only 20-30° C. above its melting temperature.

Poly(lactate), or poly(lactide), PLA, is a known polyester homopolymer comprising repeat units of lactic acid of various stereochemistry.

Polysaccharides are homopolymers and co-polymers, linear or branched, comprising hexose or pentose fragments connected via glycosyl linkages. The polysaccharides may optionally contain various additional groups such as acylamido groups, sulfate ester groups, carboxylic ester groups, alkyl and hydroxyalkyl ether groups and the like. Such additional groups may be present in polysaccharides derived from natural sources or can be artificially introduced (i.e., by acylation of cellulose). Examples of polysaccharides include acylated derivatives of cellulose and starch, as well as native or acylated chitin and pectin.

Plasticizers are chemical compounds added to a base composition comprising one or more of the above polymers with the purpose of lowering the glass transition temperature of the polymer composition, thereby making the composition more flexible and amenable to processing, e.g., by melt extrusion or molding. Plasticizers are typically used at various effective concentrations, and depending on the polymer used and desired properties of the compounded polymer formulations, plasticizers can be used at concentrations between 1 and 80% by weight of the unplasticized polymer. It is understood that, depending on the polymer and the plasticizer used, plasticizers can also confer other changes in physical and mechanical properties of the compounded polymer, as well as changes in barrier properties of the compounded polymer in respect to its permeability for various gases, water, water vapor, or organic compounds. It is also understood that one or more different plasticizers can be used in various blends with additional compounds for the preparation of an extrudable or moldable polymer composition. Such additional compounds can include various inorganic and organic filler compounds, wood dust, reinforcing fibers, dyes, pigments, stabilizers, lubricants, anti-microbial additives, and the like.

The plasticizers are typically mixed with polymer and other optional components of the base composition by mixing in various compounding equipment well known in the art at the temperatures that are above or below of the melting temperature of the polymer. The plasticizers can also be introduced with the help of an optional volatile solvent.

Ketal derivatives of levulinic acid are prepared by reacting an epoxidized unsaturated fatty acid ester with a sufficient quantity of levulinic ester in the presence of a suitable catalyst, thereby resulting in a variety of compounds that are covalent adducts between the fatty acid ester fragments and levulinic fragment.

According to one such reaction, a ketal ester compound of formula (3) is readily formed:

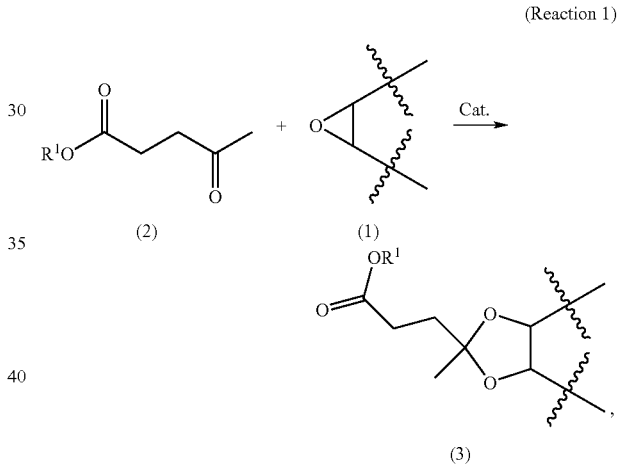

(Reaction 1)

wherein (2) is a levulinate ester, (1) is an epoxidized unsaturated fatty acid ester showing the epoxy group, (3) is the ketal ester adduct, and $R^1$ is a $C_1$-$C_{10}$ linear or branched alkyl or alkoxyalkyl.

For example, according to this reaction, a readily available ester of 9,10-epoxidized oleic ester is converted to the ketal of formula (4):

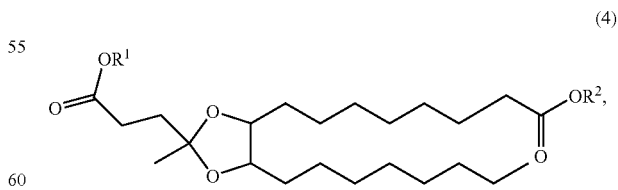

(4)

wherein $R^1$ and $R^2$ are each independently a $C_1$-$C_{10}$ linear or branched alkyl or alkoxyalkyl.

Typically, catalysts for reacting various epoxides with ketones include various acids. Such conditions are generally applicable to the reactions of levulinate esters with the epoxidized unsaturated fatty acid esters. Non-limiting examples of such catalysts include strong mineral acids, such as sulfuric, hydrochloric, hydrofluoroboric, hydrobromic acids, p-toluenesulfonic acid, camphorosulfonic acid, methanesulfonic acid, and like. Various resins that contain protonated sulfonic acid groups are also useful as they can be easily recovered after completion of the reaction. Examples of acids also include Lewis acids. For example, boron trifluoride and various complexes of $BF_3$, exemplified by $BF_3$ diethyl etherate, are also useful. Silica, acidic alumina, titania, zirconia, various acidic clays, mixed aluminum or magnesium oxides can also be used. Activated carbon derivatives comprising mineral acid, sulfonic acid, or Lewis acid derivatives can also be used. One of ordinary skill in the art can practice many variations on the part of the catalyst composition and amounts used in the compound preparation described herein.

Elevated temperatures may be used to accelerate the reaction with less reactive catalysts. However, the temperature of the reaction mixture is not critical for succeeding in making a quantity of the levulinic ketal product, as even with less active catalysts the reaction still proceeds to yield the desired compounds. Amount and type of catalyst depends on the specific chemical composition of the epoxide and levulinate ester used in the reaction and can be readily established by one skilled in the art. The reaction can be carried out in the presence of an optional co-solvent that is inert under reaction conditions and is typically removed at the end of the reaction by distillation. Typically, it is desired to use sufficient quantity of a co-solvent (or a sufficient excess of levulinate ester) to minimize cross-linking of the epoxidized fatty acid esters via ether bond formation. Non-limiting preferred examples of suitable co-solvents include saturated hydrocarbons, ethers, and carboxylic esters of simple alkanols and alkanoic acids.

Similarly to mono-epoxides, bis-epoxides of unsaturated fatty esters are converted to a mixture of stereoisomers comprising bis-ketals of levulinic ester.

When mono- or bis-epoxides of unsaturated fatty acid esters react with ethyl levulinate, the reaction of bis-epoxides of fatty acid may be accompanied by other competing reactions. These competing reactions have been found to be advantageous for making useful compounds. In particular, when a quantity of free alkanol is present, and/or when protic acidic catalysts favoring trans-esterification reactions are used, formation of an alkoxyalkanol derivative of an unsaturated fatty acid ester is favored over ketal formation. Upon use of conditions allowing for removal of alkanol after epoxide opening, the levulinoylated transesterification product of formula (5) is formed:

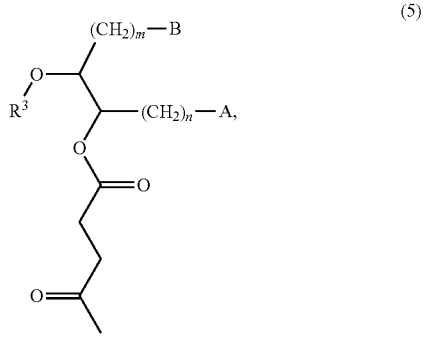

wherein $R^3$ can be a $C_{1-10}$ linear or branched alkyl or alkoxyalkyl; one of A or B is hydrogen and the other is an esterified carboxyl group; and n and m are integers each having values from 0 to 20, and the value of the sum of m+n is in the range from 8 to 21.

In a variation, known alkoxyalkanol derivatives of unsaturated fatty acid esters can be prepared by opening of the epoxide groups of an epoxidized unsaturated fatty acid ester with an alkanol. The hydroxyl groups of the alkoxyalkanol derivatives are then esterified with a levulinic ester or with free levulinic acid, or with gamma-angelicalactone thereby providing vicinal alkoxy-levulinoyl-derivatives of unsaturated fatty acid esters:

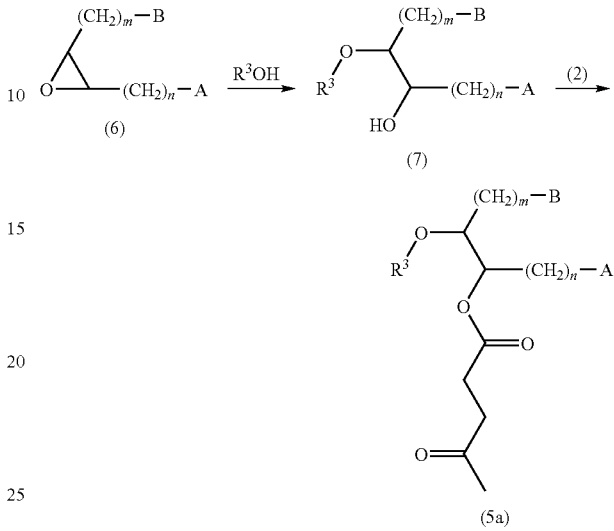

wherein (6) is an epoxidized unsaturated fatty acid ester; (7) is an alkoxyalkanol derivative; (5a) is an alkoxy-levulinoyl-derivative; $R^3$ can be a $C_{1-10}$ linear or branched alkyl or alkoxyalkyl; one of A or B is hydrogen and the other is an esterified carboxyl group; and n and m are integers each having values from 0 to 20, and the value of the sum of m+n is in the range from 8 to 21.

When bis-epoxides or tris-epoxides of unsaturated fatty acid esters having epoxy groups positioned in a close proximity to each other are used, an intra-molecular epoxide opening reaction also takes place, thereby resulting in the formation of one or more ether bonds each connecting two carbon atoms of the continuous fatty acid carbon chain. Typically, such ether bonds result in the formation of a tetrahydrofuran (major) and tetrahydropyran (minor) rings. Complex mixtures of stereoisomers of oxygenated derivatives of unsaturated fatty acid esters are then formed. For example, representative isomers of the such products from a bis-epoxide derived from a di-unsaturated fatty acid having two double bonds separated by a methylene group can have formulae (8a) and (8b):

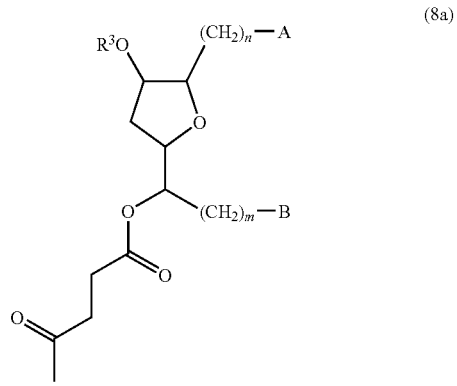

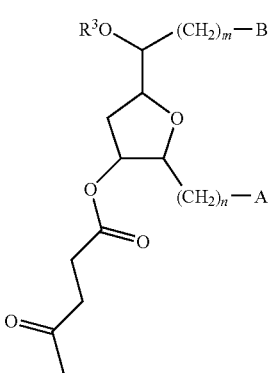

(8b)

wherein $R^3$, A, B, n, and m are as defined above.

Typically, after removal or neutralization of catalyst, and typically by distillation under reduced pressure, removal of any excess levulinate ester, solvent, and where applicable, any saturated fatty acid esters, which may be present as impurities in the epoxidized fatty acid ester starting materials, is accomplished, resulting in the formation of, a neat, transparent and practically odorless stable liquid. Depending on the specific conditions used, the liquid comprises the levulinic ketals of vicinal dihydroxy derivatives of unsaturated fatty acid esters and/or mixtures of the alkyloxy-levulinoyl-compounds. These latter compounds' can comprise ether bonds connecting two carbon atoms of the unsaturated fatty acid chain (thereby forming a tetrahydrofuran or a tetrahydropyran ring).

The levulinic adducts are useful as plasticizer compounds for PVC, poly(3-hydroxyalkanoates), poly(lactate), and various polysaccharide polymers. They are compatible with these polymers across a broad range of concentrations. By selecting various alkanol fragments present in the reactants used in the synthesis of these adducts, it is also possible to fine-tune the properties of the plasticizer not only with respect to best plasticization properties and best compatibility, but also with respect to the barrier properties of the resulting polymer, such as permeability of moisture, gases, solvent, water leaching, and odor and stain retention.

Also provided herein are a set of similar plasticizer compounds that are substantially devoid of free carbonyl groups, and thus can be blended with the levulinoyl derivatives described herein to afford desirable plasticized polymer compositions. Useful plasticizer compounds are produced by using an ester of a lower alkanoic acid instead of levulinic ester. In this embodiment, the free hydroxyl groups of alkoxyalkanol derivatives (7) are acylated with lower alkanoic acids or their anhydrides by trans-esterification, to produce esters of alkanols and lower alkanoic acids. The alkanoic acids used in this embodiment are linear or branched monocarboxylic acids having from 2 to 8 carbon atoms. Preferred examples of such acids are acetic, propionic, butyric, 2-ethylhexanoic acids. The preferred esters for trans-esterification reactions in this embodiment are esters of the above alkanoic acids and linear or branched, primary or secondary alkanols having from 1 to 4 carbon atoms. The alcohol fragment is typically selected with consideration of a desire to have a lower boiling point of the alcohol released in the trans-esterification reaction so it can be removed by distillation with ease as it is formed during the reaction. Trans-esterification is typically accomplished under ordinary conditions well known in the art and involves use of an acid or a base catalyst. The resulting alkyloxy acyloxy derivatives from mono-epoxides of mono-unsaturated fatty acid esters have formula (9):

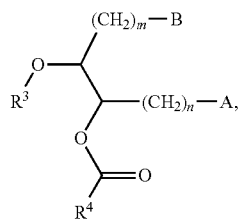

(9)

wherein $R^3$ can be a $C_{1-10}$ linear or branched alkyl or alkoxyalkyl; and $R^4$ can be a $C_1$-$C_7$ linear or branched alkyl; one of A or B is hydrogen and the other is an esterified carboxyl, group; and n and m are integers each having values from 0 to 20, and the value of the sum of m+n is in the range from 8 to 21.

Similarly to the levulinic derivatives of formulae (8a) and (8b), the resulting alkyloxy acyloxy derivatives of fatty acid esters from bis-epoxides of dienoic fatty acid esters having double bonds separated with a methylene group have representative structures (10a) and (10b):

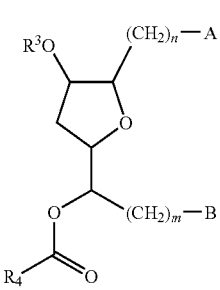

(10a)

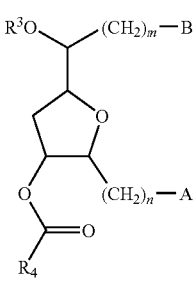

(10b)

wherein $R^3$, $R^4$, A, B, n, and m are as defined above.

The resulting alkyloxy acyloxy derivatives of fatty acid esters and lower alkanoic esters have excellent plasticizing properties similar to the levulinic ester adducts described above. Therefore, they can be used in a substantially similar fashion for polymer formulations as primary plasticizers or as mixtures with the levulinoyl derivatives disclosed herein to control presence of the free carbonyl groups in the plasticized polymer composition.

In another embodiment, where provision of a plasticizer composition for use in various PVC-containing articles is desired, synthesis of adducts of levulinic esters and epoxidized unsaturated fatty acid esters can be carried out using an epoxidized unsaturated fatty acid esters with a typical fatty acid ester contiguous carbon chain of 18 carbon atoms. Such an adduct can include compounds that contain predominantly ketals of formula (4), and, wherein bis-epoxides and tris-epoxides of unsaturated fatty acid esters are present in the starting materials, they can also be converted to levulinic ester ketal adducts exemplified by bis-ketals of formula (11) and tris-ketals of formulae (12):

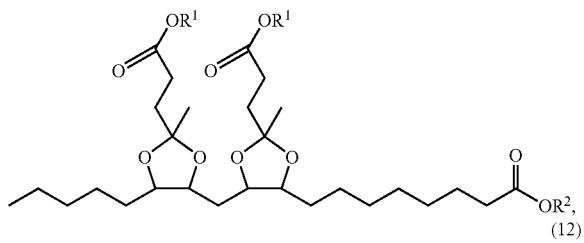

(11)

(12)

wherein $R^1$ and $R^2$ can be a $C_1$-$C_{10}$ linear or branched alkyl or alkoxyalkyl.

It is understood that in such embodiments other reaction products may be formed and may be present in various amounts. Such other reaction products may comprise, for example, stereoisomers of epoxy-ketals of formulae (13a) and (13b):

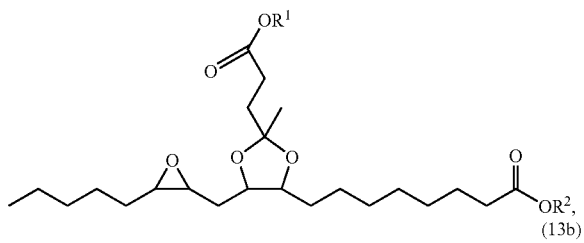

(13a)

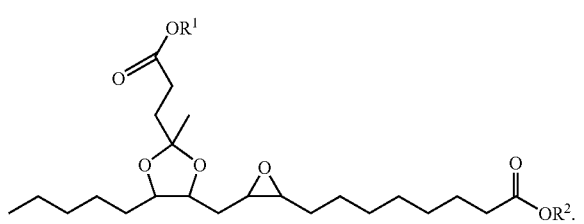

(13b)

Reaction products may also include combinations of compounds of formulae (5) though (10). Additionally, various amounts of cross-linked modified unsaturated fatty acid ester derivatives, wherein two or more contiguous carbon bonds of the unsaturated fatty acid ester are connected via an ether bond may also be present. Other compounds that may be present include various quantities of saturated fatty acid esters that do not react substantially with levulinic esters and therefore remain unchanged in the resulting product mixtures.

In further embodiments, the product mixture comprising any combination of ketal adducts produced from levulinic ester and an epoxidized unsaturated fatty acid ester (typically exemplified by ketal adducts (4), (11), (12), and (13)), and one or more saturated fatty acid esters (typically exemplified by esters of hexadecanoic or octadecanoic acids and of a monohydric alcohol $R^3$—OH), is subjected to a further treatment allowing for partial or substantially complete removal of the saturated fatty acid esters from the mixture of the ketal adducts. Such removal is typically accomplished by distilling out the esters of saturated fatty acids under reduced pressure and elevated temperature sufficient to commence distillation of the saturated esters but not the ketal adducts. Such conditions for distillation may vary, depending on temperature and vacuum used, as well as on type of distillation hardware known in the art. It has been found that ketal adducts, such as compounds (4), (11), (12), and (13) have high boiling temperatures that are typically 25-100° C. higher than those of the corresponding saturated fatty esters, and such large difference in the boiling point allows for efficient removal of saturated fatty esters using simple distillation equipment such as falling film columns or other distillation columns with a relatively low number of theoretical plates. It has been found that partial or substantial removal of the saturated fatty esters from the mixtures of adducts of levulinic esters with epoxidized unsaturated fatty acid esters results in the formation of a mixture of ketal adducts with improved plasticizing properties, improved compatibility and minimized or negligible exudation, and reduced or absent odor. It has also been found that monoketal adducts of levulinic esters with epoxidized unsaturated fatty acid esters (typically, exemplified by the ketals of formula (4)) can be effectively distilled out of the reaction mixtures comprising bis- and tris-ketal adducts (typically, exemplified by ketals of formulae (11)-(13)). Such distillations are typically performed under vacuum or under reduced pressure, and can provide for a high purity, monoketal compound in practically colorless and odorless form. Purified ketals of formula (4) were found to be excellent PVC plasticizers comparable in their PVC-plasticizing properties to the esters of sebacic and azelaic acids known in the art.

The plasticizer compounds can be used alone or in various mixtures, including many other plasticizers known in the art, such as esters of dicarboxylic acids, citric acid, and the esters of aromatic dicarboxylic acids (e.g., phthalic acid esters). Particularly useful are mixtures comprising plasticizer compounds prepared with epoxidized triglycerides with a high degree of epoxidation for plasticizing PVC. Such epoxidized triglycerides can be typically exemplified by epoxidized soybean oil and epoxidized linseed oil, while other epoxidized vegetable oils are also useful. In such formulations, the epoxidized fatty acid fragments provide a desired stabilizing effect by acing as scavengers of acidic polymer decomposition products. The plasticizer compounds are useful to make various industrial and consumer articles, including flooring materials, siding elements for exteriors and interiors of buildings, window frames, flexible and rigid pipes, tubing, reinforced hoses, artificial leather, packaging of consumer articles, interior and exterior automotive parts, electronic equipment cases, various single and multi-layered films, vinyl office supplies, and the like.

A number of embodiments of the disclosure have been described. Nevertheless, it will be understood that various modifications may be made without departing from the spirit and scope of the disclosure. Accordingly, other embodiments are within the scope of the following claims.

EXAMPLES

Example 1A 506.2 grams of a fully epoxidized soybean oil (Vicoflex 7170 brand, Arkema) was mixed with 1 L of an anhydrous methanolic solution containing 2.1 g of sodium methoxide, and the resulting mixture was magnetically stirred at room temperature (18° C.) for 6 hours. The progression of trans-esterification over time was followed by gas chromatography. After the trans-esterification reaction was found to be substantially complete, the reaction mixture was neutralized by addition of 12.8 grams of finely powdered anhydrous potassium dihydrogen phosphate, followed by stirring overnight (12 hours). The resulting mixture was filtered and the methanol was evaporated under reduced pressure using a rotary evaporator with the water bath set at 40° C. The resulting oil was dissolved in 1 L of hexanes, filtered, and the hexanes were distilled out under reduced pressure using a rotary evaporator. A clear transparent product with weak oily odor (485 g) was thereby obtained and was analyzed by GC-MS (gas-chromatography-mass-spectrometry). When using a TIC integration method, the oil was found to contain approximately 9% of methyl hexadecanoate, 5% of methyl octadecanoate, 42% of methyl-9,10-epoxy-9-octadecenoate, 40% of the isomers of methyl 9,10,-12,13-bisepoxy-9,12-octadecenoate, and small quantities of esters of other saturated and epoxidized unsaturated fatty acids.

Example 1B

Alternatively, epoxidized soybean oil fatty acids were prepared from an edible soybean oil (supplier Archer Daniels Midland Company) by trans-esterification and epoxidation reactions. 0.950 kg of the soybean oil was stirred with 0.5 L of methanol containing 6 g of sodium hydroxide at 40-45° C. for about 6 hours. The reaction mixture was neutralized by addition of 40 g of finely powdered anhydrous potassium dihydrogen phosphate, followed by stirring for 10 hours at room temperature. Methanol was distilled out of the resulting mixture under reduced pressure using a rotary evaporator and the remaining solution was mixed with 1 L of hexanes and allowed to stand in a separatory funnel for 2 hours. The lower layer (crude glycerol) was discarded. The upper layer (containing hexane-soluble materials) was collected and filtered, and the hexanes were distilled out under reduced pressure using a rotary evaporator. The resulting fatty acid methyl ester mixture (922 g, pale yellowish transparent oil with weak oily odor) was analyzed by GC-MS and was found to be in accordance with a typical soybean oil fatty acid composition. The oil was re-dissolved in 0.5 L of hexane, mixed with 100 g of aqueous 10% solution formic acid containing 500 mg of Tween 80 surfactant, and was set for intense stirring by means of a magnetic stirrer. While the mixture was continuously stiffed, 50% aqueous hydrogen peroxide (a total of 380 ml) was carefully introduced in small (20-40 ml) portions over an 8 hour period in order to maintain an exothermic reaction mixture at a temperature below the boiling point of hexanes. The progression of epoxidation was monitored by GC-MS. After epoxidation was found to be complete, the reaction mixture was separated in a separatory funnel, and the aqueous lower layer was discarded. The hexane layer was dried over anhydrous sodium sulfate, filtered and the hexane was distilled out under reduced pressure. The resulting oil (1.06 kg) was analyzed by GC-MS and was found to be practically identical to that obtained in the Example 1A.

Examples 2-5

Synthesis of epoxidized fatty acid esters was carried out according to Example 1B using olive oil, canola oil, or corn oil samples obtained from a local grocery store in place of soybean oil, or according to Example 1A using an epoxidized linseed oil (Vicoflex 7170 brand, Arkema) in place of an epoxidized soybean oil. All examples were carried out at a scale of 25% of the procedures described in Example 1, and all other materials were scaled down accordingly.

Example 6

0.2 g of epoxidized soybean oil fatty acid methyl ester prepared from soybean oil according to Example 1, and 1 g of anhydrous ethyl levulinate were dissolved in 5 ml of tent-butyl methyl ether. While the reaction mixture was stirred at room temperature by means of a magnetic stirrer, 0.01 ml of boron trifluoride etherate was added to the reaction solution, and a mildly exothermic effect was observed. After 20 min of stirring, the temperature of the reaction mixture had returned to room temperature (18° C.), an additional 0.01 ml of boron trifluoride etherate was added, and the reaction mixture was stirred for an additional 30 min, and the reaction products were analyzed by GC-MS. The reaction mixture was found to contain stereoisomers of the levulinic ketals of formulae (4) and (11) as principal reaction products:

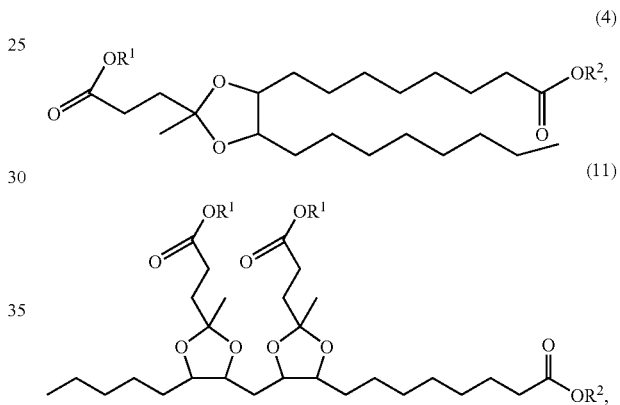

wherein $R^1$ is methyl and $R^2$ is ethyl.

Figure 1B:
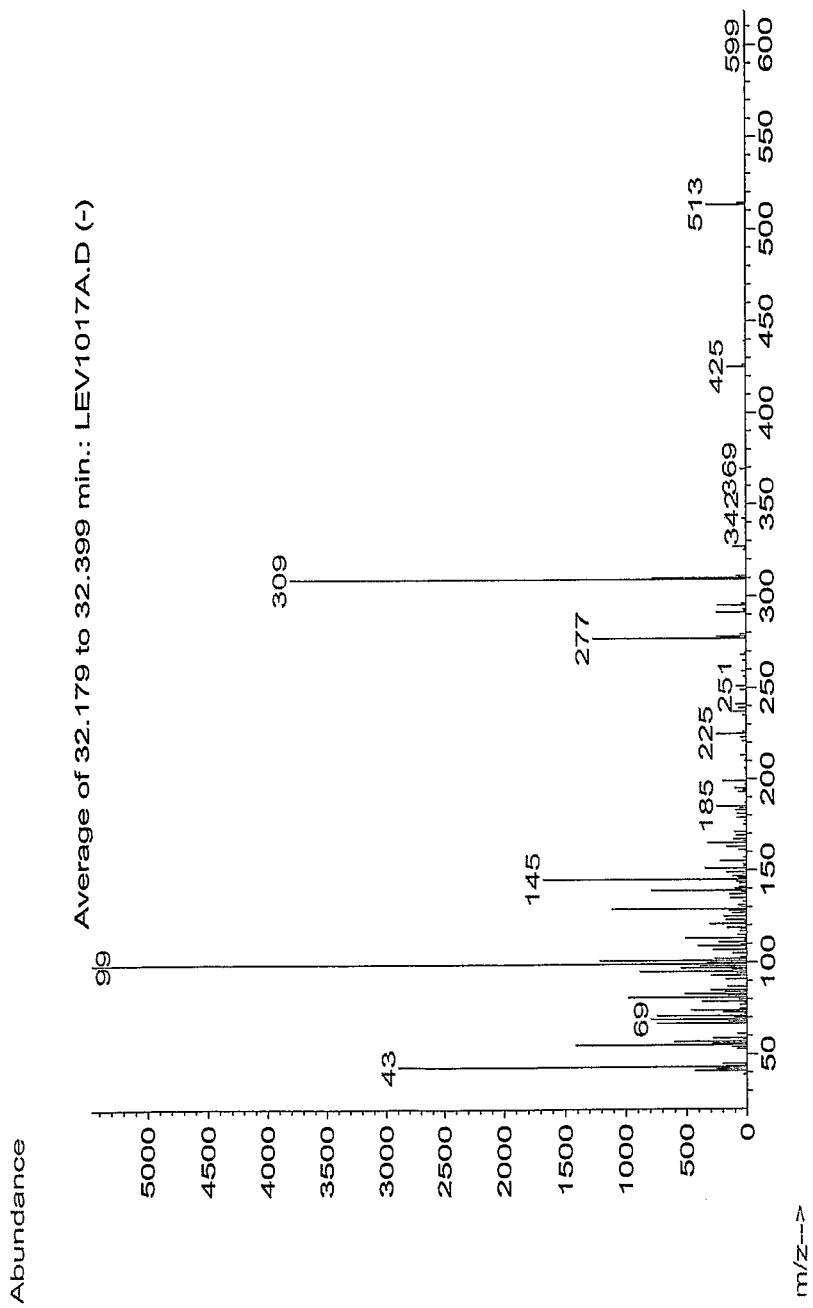

Representative mass-spectra of the isomers are shown in FIG. 1.

The reaction mixture was also found to contain excess of unreacted ethyl levulinate and unchanged saturated fatty acid ester that was present in the starting material originating from the soybean oil.

The reaction mixture was also found to contain small quantities of compound (12):

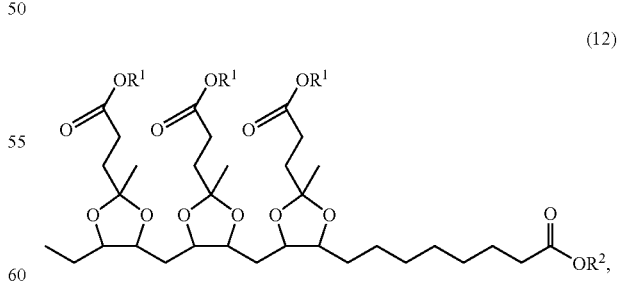

wherein $R^1$ is methyl and $R^2$ is ethyl.

Example 7

1 mL of epoxidized soybean oil fatty acid ester (prepared according to Example 1) was dissolved in 4 ml of dry methyl levulinate, and the reaction mixture was magnetically stirred under nitrogen. While the solution was stirred, the reaction was initiated by adding 0.02 mL of boron trifluoride etherate (an exothermic effect was observed). The progress of the reaction was followed by GC-MS. After 30 min, a sample was taken for GC-MS analysis (sample A), and an additional 0.02 mL of boron trifluoride etherate was added. After further stirring for 30 min, another sample was taken for GC-MS analysis (sample B).

The GC-MS analysis of sample A showed that the principal reaction products were compound (4):

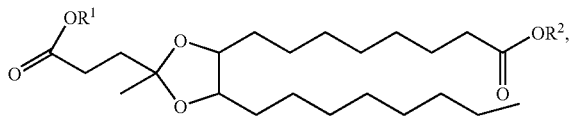

(4)

and stereoisomers of an epoxide-ketal compound having formulae (13a) and (13b):

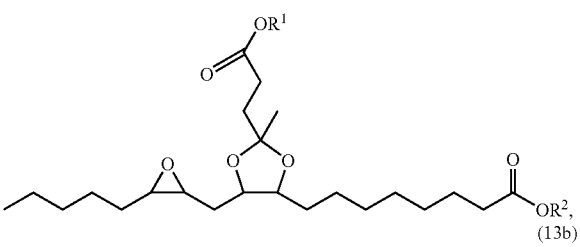

(13a)

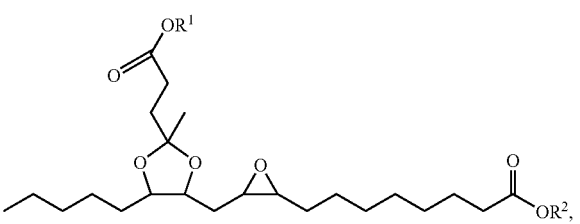

(13b)

wherein $R^1=R^2$=methyl. The GC-MS analysis of sample B showed that the principal reaction products were compound (4) and (11), and only traces of compounds of (13a) and (13b), were observed, thereby indicating that compounds (13a) and (13b) are intermediates in the formation of compound (4) resulting from a stepwise addition of levulinic ester to the bis-epoxide present in the starting material.

Figure 2B:
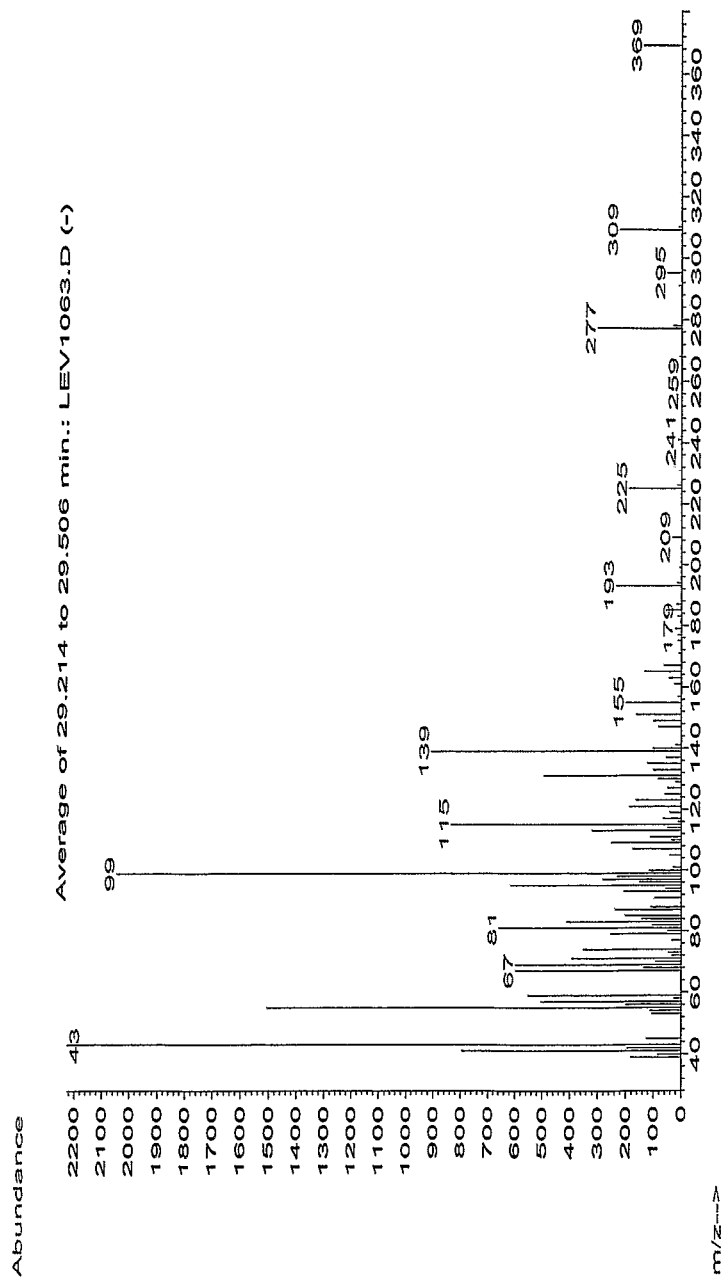
FIG. 2B is a representative IE mass-spectrum of mixture of isomers of epoxy ketal compound (13a) and (13b) (Sample A, Example 7).

Representative mass-spectra of compounds (4), (11), (13) formed in this example are shown in the FIGS. 2A and 2B.

Examples 8-12

The reactions were carried out as described in Example 7, with the exception that in place of boron trifluoride, one of the following catalysts was used: anhydrous $SnCl_2$ (50 mg), $SnCl_4$ (50 mg), $TiCl_4$ (50 mg), or p-toluene sulfonic acid (20 mg). The reactions were carried out at 60-80° C. for 3 hours. The GC characteristics and the MS-spectra of the products observed in these examples were in all respects identical to those observed in Example 7.

Example 13

The reaction was carried out as described in Example 7, except that instead of the epoxidized fatty acids of Example 1, 1.2 g of epoxidized soybean oil (Vicoflex 7170, Arkema) was used, and the amount of boron trifluoride etherate catalyst used was 0.05 ml (introduced all at once). Upon completion of the reaction, methyl levulinate was distilled under reduced pressure. The resulting oil was dissolved in 50 ml of hexanes and was washed once with 10 ml of aqueous 1% sodium fluoride, and then twice with 20 ml of water. The hexane solution was dried over anhydrous sodium sulfate, filtered, and the solvent was removed under reduced pressure. A pale yellow oil (1.32 g) was obtained that contained ketal adducts of methyl levulinate and epoxidized oil. Half of this oil (0.66 g) was dissolved in 10 mL of methanol containing 0.2% w/w of sodium methoxide, and the whole was stirred for 2 hours. The reaction mixture was then neutralized by stirring with 0.8 g of anhydrous finely powdered potassium dihydrogen phosphate for 3 hours, filtered, and the methanol was distilled out under reduced pressure. The residue was dissolved in 10 ml of hexanes and filtered. The hexanes were removed under reduced pressure, and the resulting oil (0.46 g) was analyzed by GC-MS. The composition of this oil was found to be substantially identical to that obtained in Example 7.

Examples 14-17

The synthesis was carried out according to Example 7, except that instead of epoxidized esters of Example 1, epoxidized esters prepared according to the Examples 2-5 were used. All products were found to contain varying quantities of compound (4) and (11), wherein $R^1=R^2$=methyl, in proportions reflective of abundance of epoxidized methyl-9-octadecenoate and methyl 9,12-octadecanedienoate in the starting materials. In addition, the product obtained from the methyl esters of epoxidized linseed oil fatty acids was found to contain copious amounts (approximately 35-45%) of the triketal compound (12), wherein $R^1=R^2$=methyl.

Example 18

252 grams of epoxidized esters of soybean oil fatty acids were dissolved in 745 g of dry methyl levulinate, and the whole was magnetically stirred under nitrogen, and then heated to 70° C. by means of an oil bath. Boron trifluoride etherate (1.2 ml) was introduced in 4 portions (0.3 ml each) in 20 min intervals, while the reaction was magnetically stirred and maintained at 65-70° C. by means of an oil bath. The progress of the reaction was monitored by GC-MS. After all of the catalyst was introduced, stirring was continued for 1 hr at 70° C., and then for another 1 hr at room temperature.

Methyl levulinate was distilled off under reduced pressure by means of a rotary evaporator, with the heating bath set at 105-110° C., and using a vacuum pump capable of providing an eventual 6 mm vacuum. The resulting oil was dissolved in 600 mL of hexanes and was washed with 100 mL of 2% aqueous sodium fluoride, and then washed twice with 150 ml of water. The washed hexane solution was then dried over anhydrous sodium sulfate and filtered. The filtrate was collected and hexane distilled out under reduced pressure until a constant weight has been reached. The resulting viscous oil (336 g) was of pale yellow-amber color and had a faint oily odor typical of methyl hexadecanoate. The oil was analyzed by GC-MS and was found to be practically identical in its composition to the product obtained according to Example 6.

Examples 19-22

75 g of the product obtained in Example 18 was placed in a 500-ml round bottom flask attached to a rotating Kugelrohr-type apparatus, and a vacuum was applied using a pump capable of providing an eventual vacuum of 0.1 millibar. The rotating flask containing starting material was gently heated by means of a heat gun set to provide a stream of heated air at 250° C., to allow for commencement of a steady distillation of methyl hexadecanoate and methyl octadecanoate. The distillation was stopped after approximately 5-10 g of methyl hexadecanoate and methyl octadecanoate were collected in the receiving flask, and the content of the undistilled material was evaluated for the presence of residual methyl hexadecanoate and methyl octadecanoate. The procedure of removal of methyl hexadecanoate and methyl octadecanoate was repeated several times, each time with a fresh batch of starting material. The resulting materials were found to contain principally stereoisomers of the monoketal (4) and the diketal (11), and small quantities of triketal (12), wherein $R^1=R^2$=methyl. The resulting mixtures of compounds were also found to contain small amounts of methyl hexadecanoate and methyl octadecanoate in varying proportions. The total content of methyl hexadecanoate and methyl octadecanoate, when taken together, was found to be less than 0.1% (Example 19), approximately 1.5% (Example 20), approximately 2.9% (Example 21), and approximately 5.1% (Example 22) by weight.

Example 23

96 grams of the mixture of compounds prepared according to Example 19, containing predominantly ketals (4) and (11), wherein $R^1=R^2$=methyl, were placed in a 500 ml round bottom flask attached to a rotating Kugelrohr-type apparatus, and a vacuum was applied using a pump capable of providing an eventual vacuum of 0.1 millibar. The rotating flask containing starting material was gently heated by means of a heat gun set to provide a stream of heated air at 350° C. A gentle distillation was commenced, and approximately 32 grams of distillate was collected into the receiving vessel, and the distillation was stopped by turning the heat off, and the materials were allowed to cool to room temperature under vacuum. The distillate (Example 23A) was a practically colorless and odorless oil. It was analyzed by GC-MS and was found to be 96% pure monoketal compound (4), wherein $R^1=R^2$=methyl. Traces of compound (11), (13a) and (13b) were also found (Example 23A).

The residual oily material remaining in the distillation flask (Example 23B) was analyzed by GC-MS and was found to contain approximately 80% of the stereoisomers of diketal compound (11), 12% of the monoketal (4), and small quantities of the triketal (12), wherein $R^1=R^2$=methyl.

Examples 24-28

16 grams of the mixture containing ketal (4) and diketal (11), $R^1=R^2$=methyl, as principal congeners, prepared according Example 19, was dissolved in 40 ml of one of the following:

(24) absolute ethanol with approximately 0.2% w/w of sodium ethoxide,
(25) anhydrous n-butanol with approximately 0.2% w/w of sodium n-butoxide,
(26) anhydrous isobutanol with approximately 0.4% of sodium isobutoxide,
(27) anhydrous isoamyl alcohol with 0.3% of sodium 3-methylbutoxide,
(28) 2-ethylhexyl alcohol with 0.3% of sodium 2-ethylhexoxide.

The solutions were stirred for 12 hours by means of magnetic stirring at room temperature (26° C.). Progression of the trans-esterification was monitored by analyzing small aliquots of the reaction mixtures by GC-MS. Mixtures of compounds (4) and (11), wherein $R^1$ or $R^2$ are each methyl and wherein one of $R^1$ or $R^2$ is methyl and the other is ethyl, n-butyl, isobutyl, isoamyl or 2-ethylhexyl were detected.

Figure 3A:
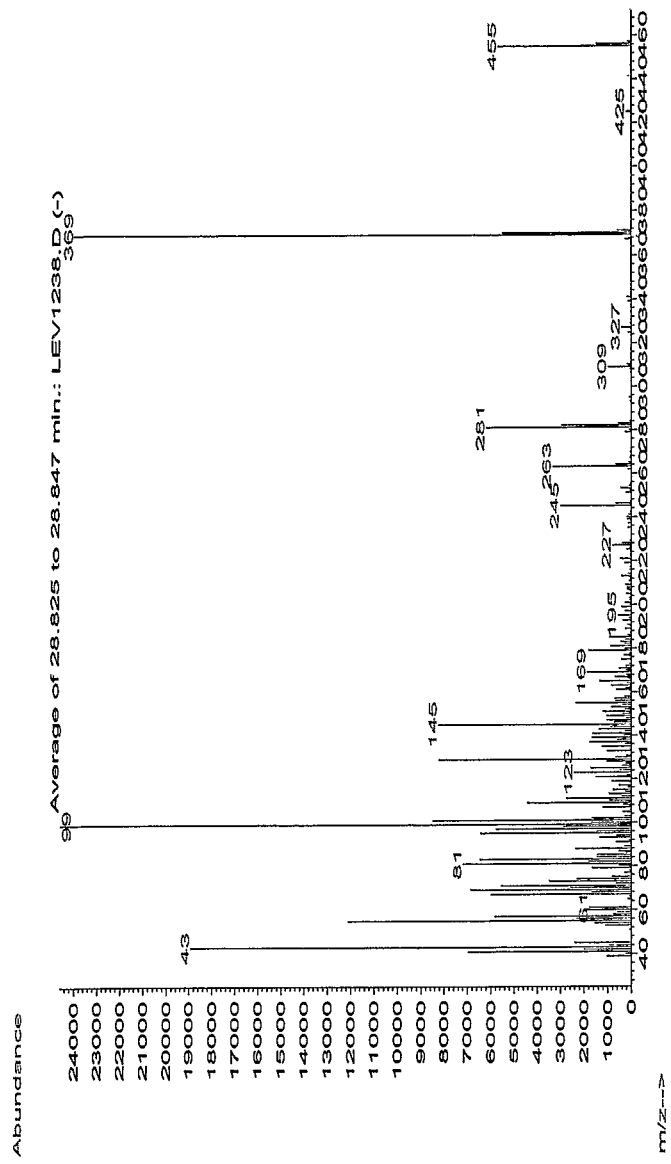
FIG. 3 shows a representative IE mass-spectrum of mixture of isomers of monoketal compound (4) wherein $R^1$=$R^2$=ethyl (Example 24) (FIG. 3A), and a representative IE mass-spectrum of mixture of isomers of diketal compound (11) wherein $R^1$=$R^2$=ethyl (Example 24) (FIG. 3B).
Figure 3B:
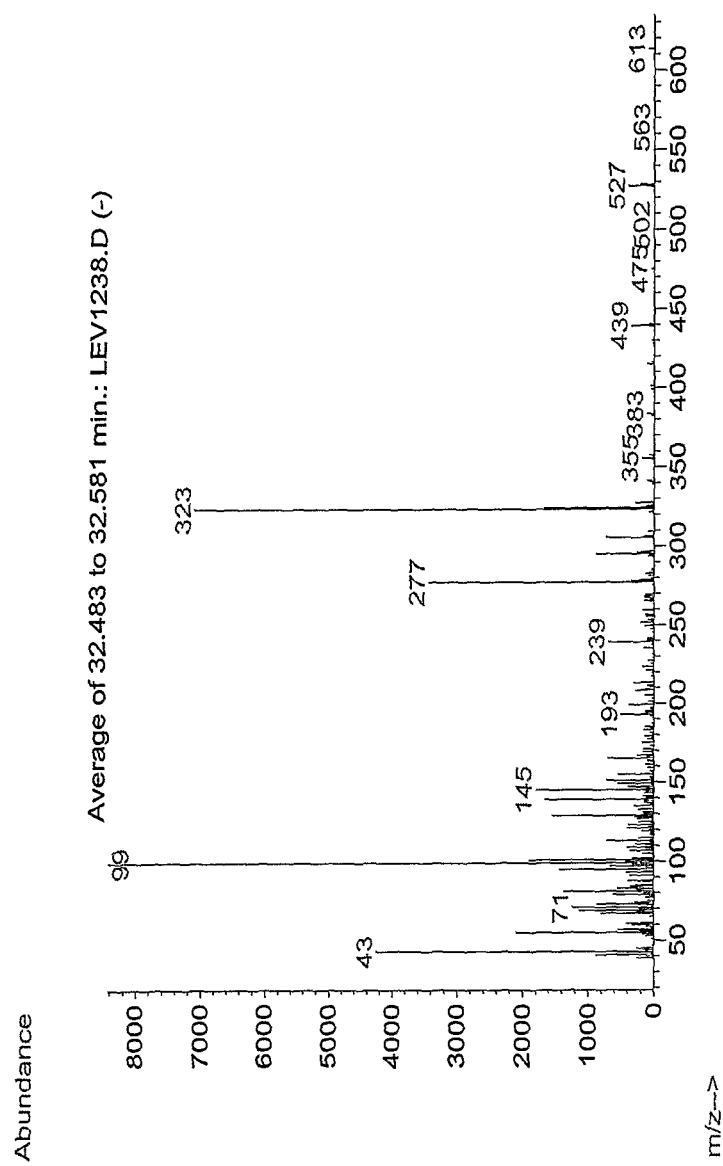
Figure 4A:
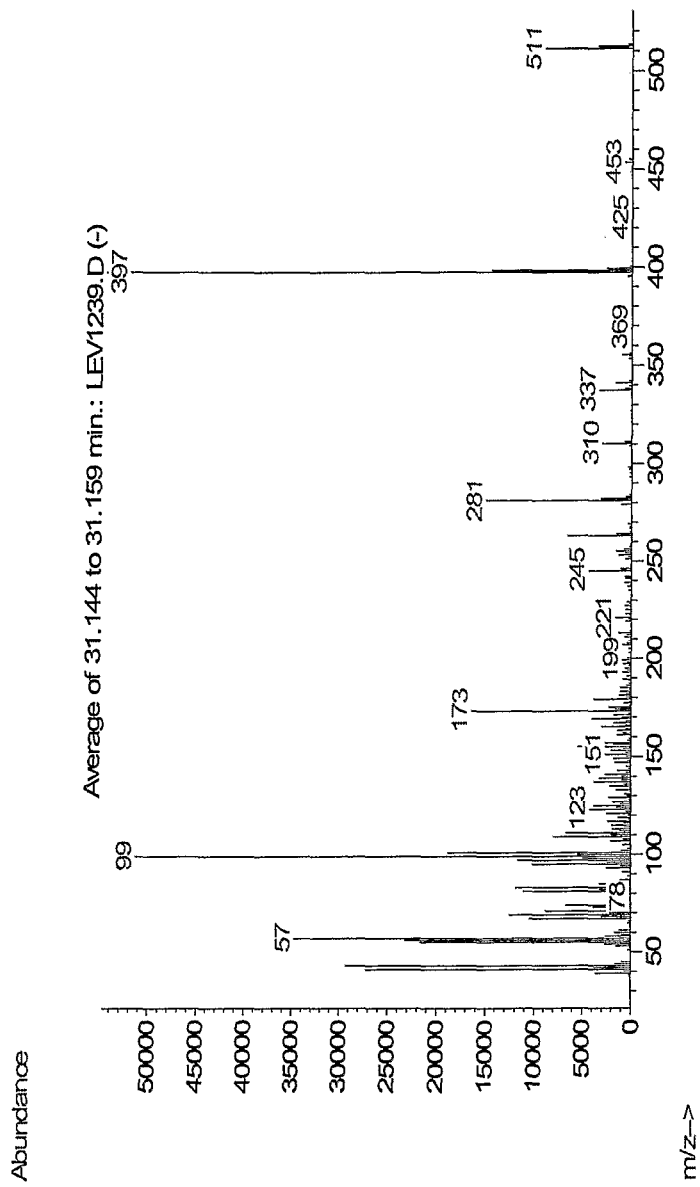
FIG. 4 is a representative IE mass-spectrum of mixture of isomers of monoketal compound (4) wherein $R^1$=$R^2$=n-butyl (Example 25) (FIG. 4A), and a representative IE mass-spectrum of mixture of isomers of diketal compound (FIG. 4B) wherein $R^1$=$R^2$=n-butyl (Example 25).
Figure 4B:
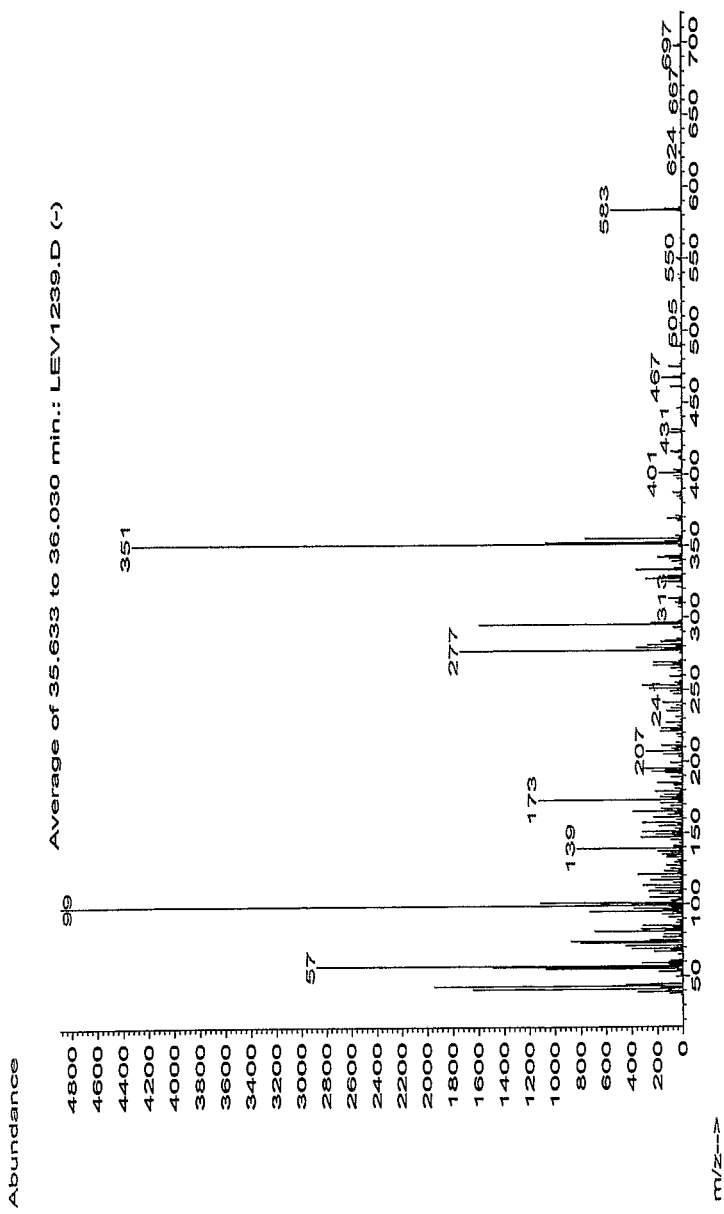

Representative mass-spectra of monoketal (4) and diketal (11) prepared and observed in Examples 24 and 25 are shown in the FIGS. 3 and 4, respectively.

After the trans-esterification reaction was substantially complete, as judged by GC-MS analysis, the reaction mixtures were neutralized by the addition of 0.4-0.5 g of powdered anhydrous potassium dihydrogen phosphate, followed by a vigorous stirring at room temperature for 24 hours. The solutions were then filtered, and excess alcohol from each sample was distilled out under reduced pressure on a rotary evaporator until a constant weight for each sample was reached. The resulting oily products were analyzed by GC-MS and were found to contain predominantly compounds (4) and (11), wherein $R^1=R^2$, and $R^1$ and $R^2$ are selected from ethyl, n-butyl, isobutyl, isoamyl, 2-ethylhexyl.

Examples 29-40

Trans-esterification reactions were carried out according to Examples 24 and 25, except that the starting materials comprising levulinic ketal adducts (4) and (11) were prepared according to the Examples 18, 20, 21, 22, 23A and 23B, the resulting product mixtures had $R^1=R^2$ selected from ethyl or n-butyl and contained various small amounts of ethyl or n-butyl esters of hexadecanoic or octadecanoic acids in quantities consistent with their abundance in the starting materials prior to the trans-esterification.

Example 41

Plasticized PVC compositions comprising compounds (4) and (11) were prepared. Samples of neat plasticizer compound mixtures comprising varying amounts of ketals (4) and (11), prepared according to Examples 18-40, were thoroughly pre-mixed in 20-ml glass vials with dry PVC powder (average $M_n$ ca. 55,000, average $M_w$ 97,000, inherent viscosity 0.92, relative viscosity 2.23, supplier Sigma-Aldrich Company, Cat. No. 34,677-2), in proportions providing for a final plasticizer content of 20%, 40 or 60% by weight. Bis-(2-ethylhexyl)phthalate, bis-(2-ethylhexyl)sebacate and epoxidized soybean oil (Vicoflex brand, Arkema) were used as reference plasticizers. Each of the resulting mixtures were individually fed into a pre-cleaned miniature twin-screw mixer-extruder chamber of a Daca Microcompounder (Daca Instruments) under nitrogen, with the mixing chamber heated to 160° C., and the motor speed set at 100 rpm. The mixture was then mixed for about 5 minutes. The resulting melt was then extruded out of the mixing chamber as a flexible rod (diameter 3 mm), which was immediately cooled to room temperature in ambient air.

Glass transition temperature data (by differential scanning calorimetry), and plasticizer exudation data were collected using plasticized PVC specimens cut from the extruded rods.

All compound mixtures comprising compounds (4) and/or (11) were found to have satisfactory plasticizing properties, as judged by observation of lowered glass transition temperatures in comparison with the non-plasticized polymer. The compounds were also found to have excellent polymer compatibility properties, with a minimal or negligible exudation upon a stress exudation test. The plasticizing efficacy of the compound mixtures prepared according to Examples 18-40 were found to be superior to, or comparable with that of bis-(2-ethylhexyl)phthalate. PVC compatibility and exudation properties were also found to be superior to that of epoxidized soybean oil and bis-(2-ethylhexyl)phthalate at the plasticizer concentrations tested.

An optimal combination of the plasticizing efficacy and compatibility was observed under the conditions tested when mixtures of the plasticizer compound comprised predominantly monoketal (4) and/or diketal (11) having $R^1=R^2=$ethyl or n-butyl. Furthermore, the samples of the mixtures of plasticizers comprising monoketal (4) and diketal (11), wherein the concentration of alkyl hexadecanoate and alkyl octadecanoate was at about 5% or less by weight of the plasticizer, exhibited better compatibility of the plasticizer with PVC and showed virtually no exudation as compared to those samples in which the concentration of alkyl hexadecanoate and alkyl octadecanoate was in excess of about 5%.

Example 42

Samples of plasticized PHB, (poly(3-hydroxybutyrate, natural origin, Tm 172° C., supplied by Sigma-Aldrich Cat. No. 36,350-2) were prepared according to Example 41, with the exception that the temperature of the mixing chamber was set at 180° C., mixing time was set at 3 min, and mixtures of the plasticizer compounds of Examples 18-40 comprising ketals (4) and (11) were tested at 5, 10, 20 and 30% by weight. Mixtures of plasticizer compounds wherein $R^1=R^2=$methyl or ethyl were found to have satisfactory plasticizing efficiency and compatibility under the conditions tested when the concentration of plasticizer was at or below about 20% by weight, and when the content of the corresponding alkyl hexadecanoate and alkyl octadecanoate was at or below about 1.5% by weight of the plasticizer.

Example 43

Plasticized polymer compositions were prepared according to Example 42, except that a cellulose acetate polymer with 39.8% acetyl content and $M_n$ ca. 30,000 (Sigma-Aldrich Cat. No. 18,095-5) was used. The results obtained were similar to those obtained with the PHB polyester used in Example 42.

What is claimed is:

1. A compound having the formula:

wherein:
$R^1$ is a $C_1$-$C_{10}$ linear or branched alkyl or alkoxyalkyl;
one of A or B is hydrogen and the other is an esterified carboxy group; and
m and n are independently integers from 0 to 20, wherein the sum of m+n is in the range from 8 to 21.

2. A compound having the formula:

wherein:
$R^1$ and $R^2$ are independently a $C_1$-$C_{10}$ linear or branched alkyl or alkoxyalkyl.

3. A compound having the formula:

wherein:
$R^1$ and $R^2$ are independently a $C_1$-$C_{10}$ linear or branched alkyl or alkoxyalkyl.

4. A compound having the formula:

wherein:
$R^1$ and $R^2$ are independently a $C_1$-$C_{10}$ linear or branched alkyl or alkoxyalkyl.

5. A compound having the formula:

wherein:
$R^1$ and $R^2$ are independently a $C_1$-$C_{10}$ linear or branched alkyl or alkoxyalkyl.

6. A compound having the formula:

wherein:
$R^1$ and $R^2$ are independently a $C_1$-$C_{10}$ linear or branched alkyl or alkoxyalkyl.

7. The compound of any one of claims 2-6, wherein $R^1$ and $R^2$ are independently selected from the group consisting of methyl, ethyl, n-butyl, isobutyl, isoamyl, and 2-ethylhexyl.

8. The compound of claim 7, wherein $R^1$ and $R^2$ are independently selected from the group consisting of methyl, ethyl, and n-butyl.

9. A method for preparing a compound of any one of claims 1 and 2-6, or mixtures thereof, the method comprising:
  a) providing an epoxidized fatty acid ester derivative and one or more of levulinate ester, levulinic acid and angelicalactone;
  b) effecting the reaction between the compounds of a) in the presence of an acid catalyst, wherein the reaction results in the formation of a compound of any one of claims 1 and 2-6, or mixtures thereof.

10. A plasticized polymer composition comprising:
  a) a base polymer; and
  b) a compound of any one of claims 1 and 2-6.

11. The plasticized polymer composition of claim 10, wherein the base polymer is selected from the group consisting of a vinyl chloride polymer, a poly(3-hydroxylalkanoate) polymer, and a polysaccharide polymer.

12. The plasticized polymer composition of claim 11, wherein the base polymer is vinyl chloride polymer.

* * * * *